(12) United States Patent
Hasegawa

(10) Patent No.: US 6,584,169 B2
(45) Date of Patent: Jun. 24, 2003

(54) X-RAY MAPPING ANALYSIS METHOD

(75) Inventor: Kiyoshi Hasegawa, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 10/153,508

(22) Filed: May 22, 2002

(65) Prior Publication Data
US 2002/0186810 A1 Dec. 12, 2002

(30) Foreign Application Priority Data
Jun. 8, 2001 (JP) .......................... 2001-173981

(51) Int. Cl.[7] .......................................... G01N 23/223
(52) U.S. Cl. ...................................................... 378/45
(58) Field of Search ................................. 378/44–50

Primary Examiner—Craig E. Church
(74) Attorney, Agent, or Firm—Adams & Wilks

(57) ABSTRACT

In order to acquire typical X-ray spectra by dividing automatically dividing contained matter and regions where the density thereof differs into groups in X-ray mapping analysis, measurement starts with the spectra database empty, a designated location within the sample is irradiated with a primary beam by the primary beam control means, the sample is irradiated with the primary beam for a fixed period of time in order to acquire a measurement spectrum, the X-ray spectrum obtained through measurement and X-ray spectra in the spectra database are compared by the X-ray comparison means, the X-ray spectrum obtained through measurement is added to the database when no matching X-ray spectra exists in the database, and measurement is repeated at a designated measurement point.

7 Claims, 5 Drawing Sheets

FIG.5

| NOTED ELEMENT | Cu | Sn |
|---|---|---|
| ROI(keV) | 7.8-8.3 | 24.9-25.5 |
| DETERMINE DIFFERENCE IN X-RAY INTENSITY | 100 cps CHANGE | 50 cps CHANGE |
| FORMULA | ABSOLUTE VALUE OF (Cu1 INTENSITY−Cu2 INTENSITY) | ABSOLUTE VALUE OF (Sn1 INTENSITY−Sn2 INTENSITY) |

FIG.6

| NOTED ELEMENT | Cu | Sn |
|---|---|---|
| ROI(keV) | 7.8-8.3 | 24.9-25.5 |
| DETERMINE CHANGE IN X-RAY INTENSITY | CHANGE OF 30% | CHANGE OF 30% |
| FORMULA | ABSOLUTE VALUE OF (Cu1 INTENSITY÷Cu2 INTENSITY) | ABSOLUTE VALUE OF (Sn1 INTENSITY÷Sn2 INTENSITY) |

FIG.7

| NOTED ELEMENT | Cu | Sn |
|---|---|---|
| ROI(keV) | 7.8-8.3 | 24.9-25.5 |
| DETERMINE CHANGE IN X-RAY INTENSITY RATIO | CHANGE OF 10% | CHANGE OF 10% |
| FORMULA | ABSOLUTE VALUE OF {Cu1 INTENSITY÷(Cu1+Sn1 INTENSITY)}−{Cu2 INTENSITY÷(Cu2+Sn2 INTENSITY)} | ABSOLUTE VALUE OF {Sn1 INTENSITY÷(Cu1+Sn1 INTENSITY)}−{Sn2 INTENSITY÷(Cu2+Sn2 INTENSITY)} |

X-RAY MAPPING ANALYSIS METHOD

BACKGROUND OF THE INVENTION

1. Field of the Invention

The present invention relates to an X-ray mapping device for detecting X-rays and investigating elemental distribution.

2. Description of Related Art

In a first method of the related art, a noted element and an X-ray energy region for calculating X-ray intensity of the noted element are designated in advance, information for the measured location and the X-ray intensity acquired from the measured spectra is accumulated, and distribution analysis is carried out using X-ray intensity magnitude information.

In a second method, X-ray spectra for all measurement points are saved, and analysis is performed after measurement using X-ray spectra.

However, in the first analysis method, when elements are present within the sample for which elements have not been estimated in advance, there is the substantial drawback that information regarding the presence and distribution of this element has to be disregarded.

In the second method, all of the information resources are filled up to a maximum in order to save all of the measured spectra and there is the disadvantage that an extremely long time is required in order to analyze all of the spectra after measurement.

It is therefore the object of the present invention to provide data for X-ray mapping analysis in such a manner that regions of the sample that contain different elements and regions where the concentration of contained materials is different are automatically split up into different groups so as to enable detailed analysis immediately after measurement.

SUMMARY OF THE INVENTION

The present invention adopts the following means in order to resolve the aforementioned problems.

An X-ray mapping analysis method for putting typical spectra existing in a sample into a database employs an X-ray mapping device comprising: excitation means for irradiating a sample with a primary beam in order to excite X-rays; primary beam control means for controlling the beam from front to back and from left to right with respect to the sample; X-ray detecting means for measuring X-ray intensity while discriminating energy of X-rays from the sample; spectra comparison means for comparing two X-ray spectra obtained by the X-ray detecting means; and a spectra database capable of registering X-ray spectra during measurement, and the method comprises the steps of: starting measurement with the spectra database empty; irradiating a designated location within the sample with a primary beam using the primary beam control means; irradiating the sample with the primary beam for a fixed period of time in order to acquire a measurement spectrum; comparing the X-ray spectrum obtained through measurement and X-ray spectra in the spectra database using the X-ray comparison means; adding the X-ray spectrum obtained through measurement to the database when no matching X-ray spectra exists in the database; and repeating measurement at a designated measurement point.

In this X-ray mapping analysis method, numbers are assigned to X-ray spectra within the database, results determined by the comparison means are saved as database numbers, and analysis results are displayed using database number information and measurement position information so that distribution of elements can be confirmed visually.

With this mapping analysis method, X-ray spectra of little variation are obtained by performing measurements again for a long period of time at the same location and storing spectra acquired at such times in the database when no matching X-ray spectra exist within the database.

In a first method for the spectra comparison means of the X-ray mapping analysis method, the spectra comparison means designates a noted element and an X-ray energy region for calculating X-ray intensity of the noted element in advance, compares X-ray intensity of each element of the X-ray spectra in the database and the X-ray intensity of each element in the measured spectra, and determines spectra to be different when change is in excess of or equal to a reference.

In a second method for the spectra comparison means of the X-ray mapping analysis method, the spectra comparison means designates a noted element and an X-ray energy region for calculating X-ray intensity of the noted element in advance, calculates an intensity ratio of a total value of X-ray intensity of a noted element and an X-ray intensity for each element for the X-ray spectra in the database, and, for the measured spectra, calculates a ratio of the total value of X-ray intensity of the noted element and the X-ray intensity of each element, compares the intensity ratio for the same element, and determines that spectra are different spectra when change is equal to or in excess of a reference value.

In a third method for spectra comparison means for an X-ray mapping analysis method, an X-ray mapping device is characterized by spectra comparison means enumerating energy existing at peaks of X-ray spectra of the data base and of measured spectra and determining different spectra using the presence or absence of each peak.

In this X-ray mapping analysis method, the primary beam is an X-ray beam.

BRIEF DESCRIPTION OF THE DRAWINGS

FIG. 5 shows a method for comparing X-ray spectra using differences in X-ray intensity.

FIG. 6 shows a method for comparing X-ray spectra using ratios of changes in X-ray intensity.

FIG. 7 shows a method for comparing X-ray spectra using X-ray intensity of a noted element and a total value for the X-ray intensity of a noted element.

DETAILED DESCRIPTION OF THE INVENTION

First Embodiment

The following is a description, with reference to the drawings, of an embodiment that is a practical implementation of the present invention.

First, a description of an analysis procedure that is the basis of the present invention is described.

Figure 1:
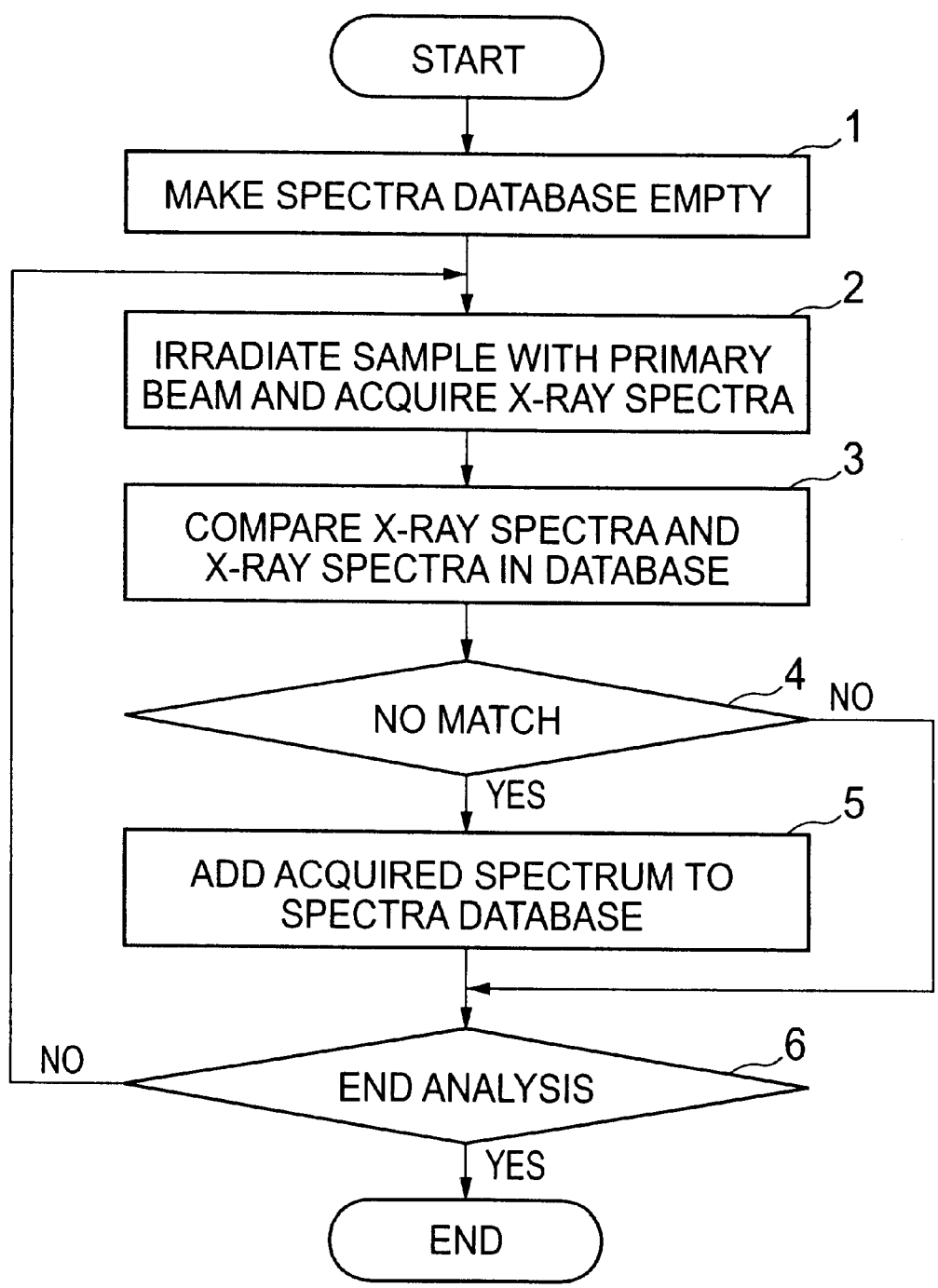
FIG. 1 is a view showing the flow with which the present invention is implemented.

In analysis procedure 1 in FIG. 1, a spectra database for accumulating typical X-ray spectra is emptied. In analysis procedure 2, the position of a primary beam irradiating the sample is controlled and the sample is irradiated with a primary beam. X-ray spectra are then accumulated for a period of time designated by the X-ray detection means. In analysis procedure 3, acquired X-ray spectra and X-ray spectra in the spectra database are compared by the comparison means. When the first measurement is carried out, no X-ray spectra have as-yet been accumulated in the spectra database and it is therefore determined that matching X-ray spectra do not exist. When measurements are carried out from the second time onwards, processing is carried out to make comparisons with all of the X-ray spectra stored in the spectra database. Analysis procedure 4 is for performing branching processing using the results of the determination of analysis procedure 3. When it is determined that there are no matching X-ray spectra, analysis procedure 5 is proceeded to, and when it is determined that there are matching X-ray spectra, analysis procedure 6 is proceeded to. In analysis procedure 5, the X-ray spectrum acquired in analysis procedure 2 is added to the spectra database. In analysis procedure 6, analysis procedure 2 is proceeded to when the analysis is not yet complete, and when complete this measurement operation is ended.

By carrying out an analysis operation using the above procedures, typical X-ray spectra for regions of the sample that contain different materials and regions where the concentration of contained materials is different within the analysis sample can automatically be put into the database.

Secondly, an example of a device for implementing the present invention is described.

Figure 2:
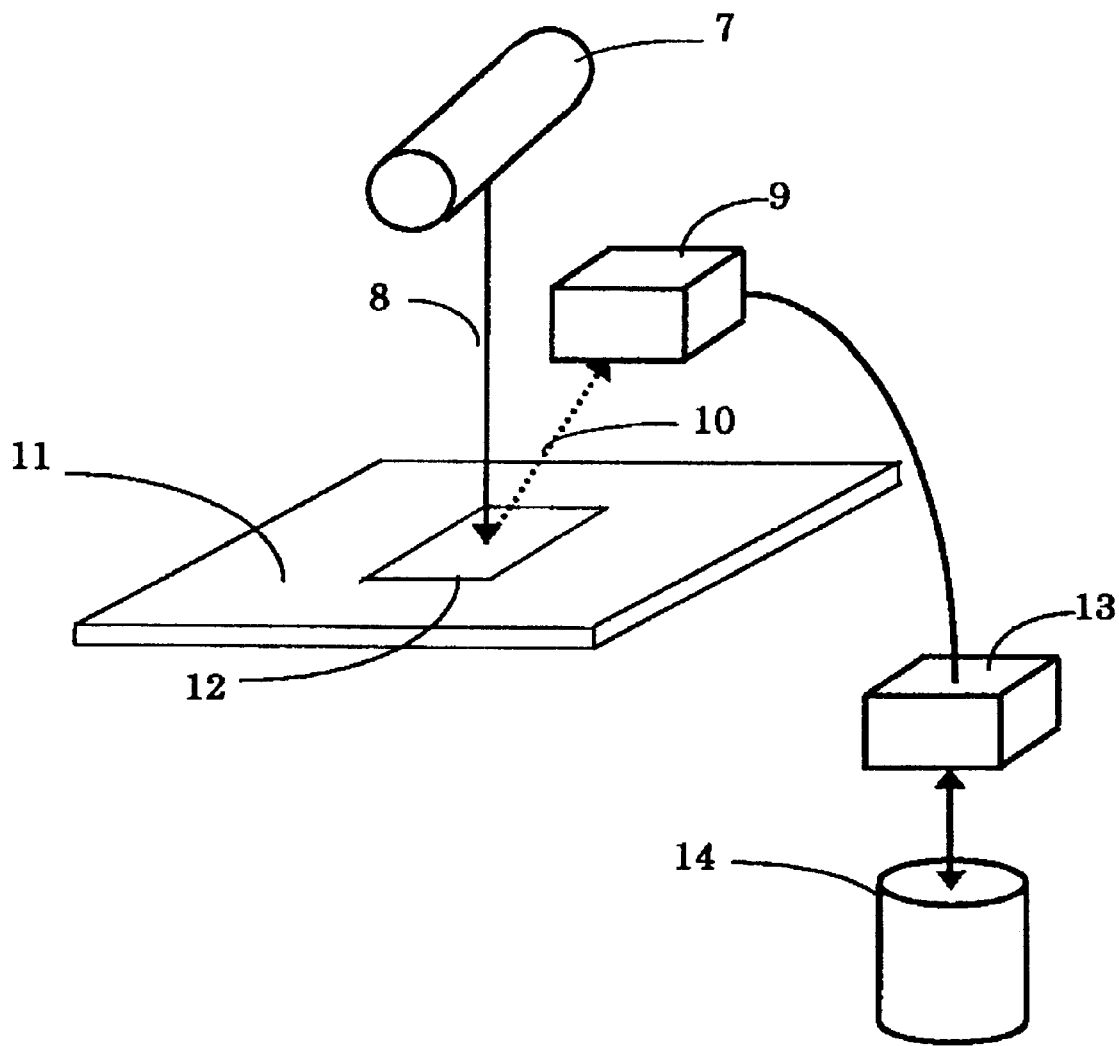
FIG. 2 is a view showing a structural example of a device for implementing the present invention.

An example of a device using primary X-rays is described in FIG. 2.

An X-ray generating device is used as excitation means 7 irradiating a primary beam. A collimator focusing X-rays is installed as necessary. A primary beam 8 that irradiates a sample to be measured 12 is an X-ray beam. Fluorescent X-rays are emitted as X-rays 10 obtained from the sample from the sample to be measured 12, an X-ray detector such as an SiLi detector etc. capable of energy discrimination is used as X-ray detecting means 9, and X-rays are detected.

X-ray spectra comparison processing is carried out using a computer system and software as means 13 for comparing spectra and a hard disc is used as means 14 for storing the spectra database. An XY stage is used as a sample stage for controlling the relative positions of the sample and the primary beam.

Figure 3:
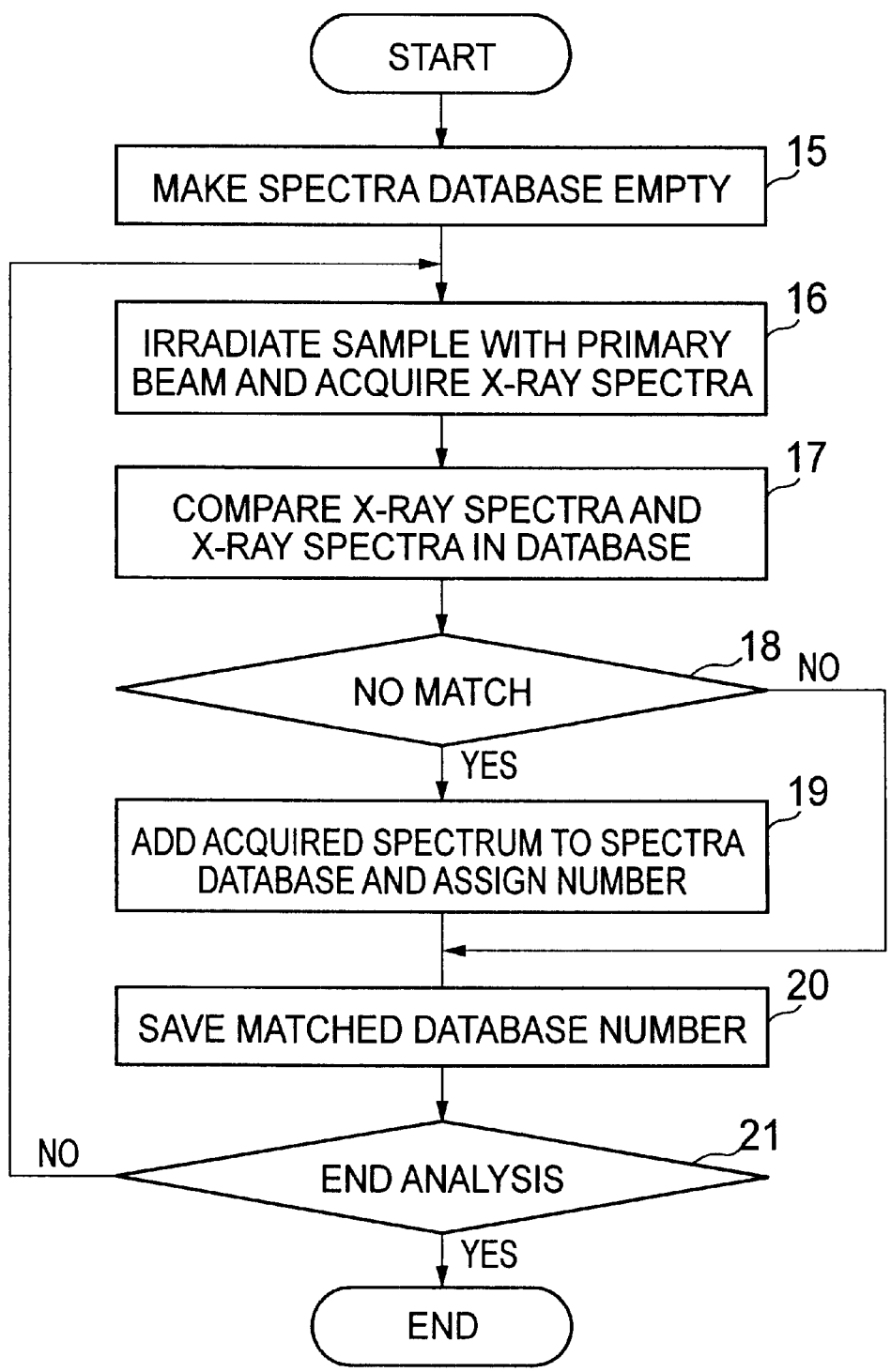
FIG. 3 is a view showing the flow for saving database numbers.

Thirdly, in the analysis procedure shown in FIG. 3 is a procedure for determining in what manner regions having characteristics stored in the database spectra are distributed.

Regarding the analysis procedure in FIG. 1, when an X-ray spectrum is saved to the spectra database in analysis procedure 19, numbers are given to each spectra, and prior to the final determination, a process is added to save the numbers of spectra in the spectra database that match with each of the measured spectra in analysis procedure 20.

In the analysis operation using the above procedure, it is possible to determine in what manner regions having characteristics stored in the database spectra are distributed.

In subsequent processing, it is then possible to confirm distribution visually, as the relationship between information for the measurement position and the spectra database number is displayed.

Figure 4:
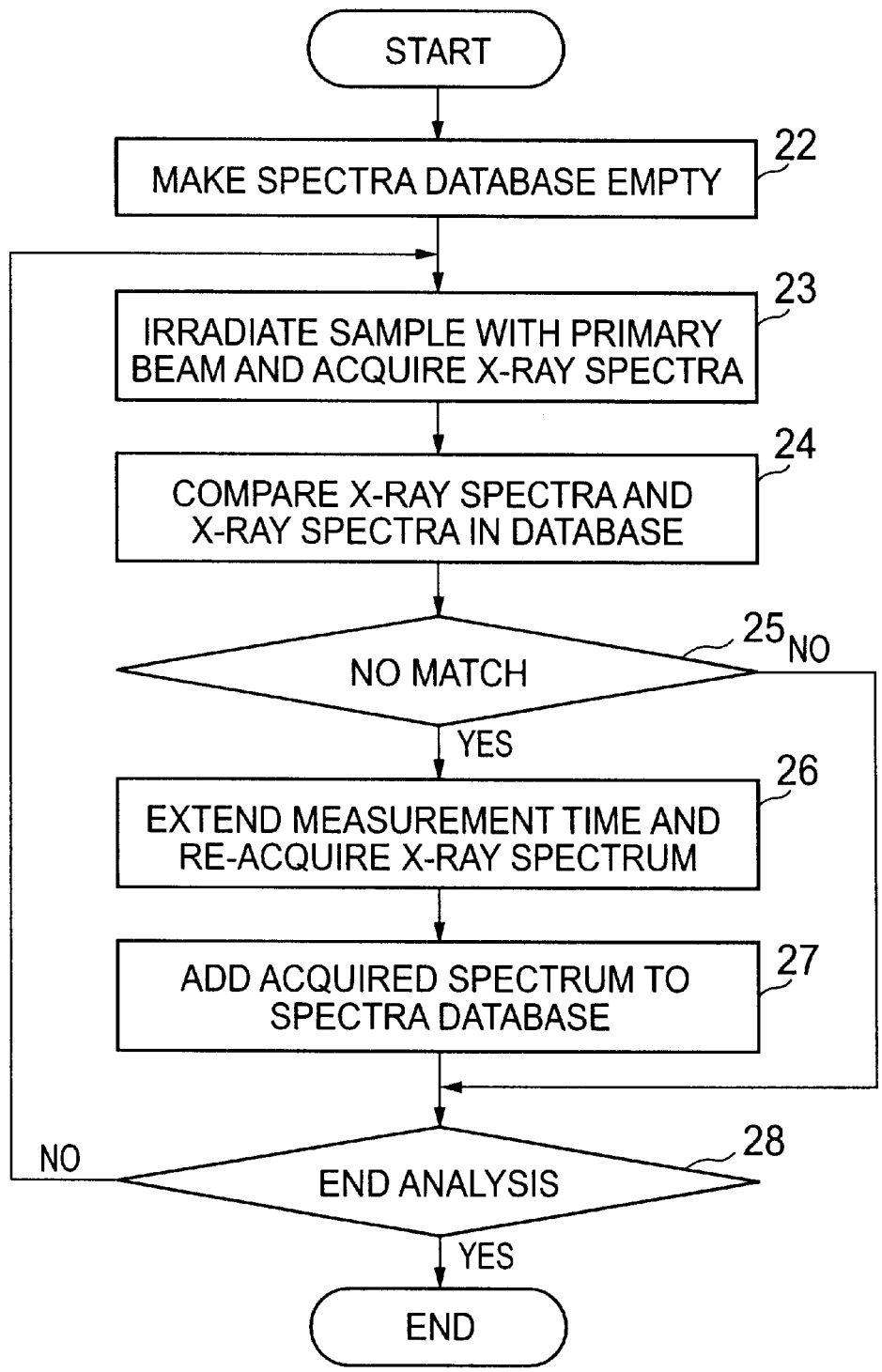
FIG. 4 is a view showing the flow for when X-ray spectra are re-acquired over a long period of time when an X-ray spectrum is encountered that does not have a match in the database.

Fourthly, the distribution procedure shown in FIG. 4 is a distribution procedure for obtaining X-ray spectra with little variation in the spectra database.

When there is no matching X-ray spectra in the spectra database in the analysis procedure in FIG. 1, a process is added to again acquire the X-ray spectra using analysis procedure 26 while lengthening the measuring time.

X-ray spectra having little variation are therefore acquired in the spectra database by carrying out the analysis operation using the above procedures.

For example, when the primary beam is an X-ray, measurement is performed for 10 seconds to acquire an X-ray spectra by irradiating the sample with a primary beam in analysis procedure 23. Measurement is carried out for 100 seconds in analysis procedure 26. If the presence or absence of contained materials is determined, a sufficient determination can be made in approximately 10 seconds, and spectra are saved in the database in 100 seconds when the purpose is to accurately calculate concentration. X-ray spectra with little variation can therefore be obtained in an efficient manner because measuring time can be changed in a selective manner.

Fifthly, a description is given of means for comparing X-ray spectra.

In a first method for the comparing means, a method is described where a noted element and an X-ray energy region for calculating X-ray intensity for the noted region are designated, and the X-ray spectra are compared.

This method is effective when the materials contained in the sample are known in advance.

As shown in FIG. 5, an example is described in the following where determinations are executed taking note of copper and tin.

The noted elements are copper and tin, and the X-ray energy region for calculating X-ray intensity of copper is taken to be 7.8 to 8.3 keV. The X-ray energy region for calculating X-ray intensity of tin is taken to be 24.9 to 25.5 keV. A reference for comparing differences in X-ray intensity is then designated as a comparison threshold value. In this example, the copper is taken to be 100 CPS, the tin 50 CPS, and when differences greater than or equal to this are confirmed, the results of the X-ray spectra comparison are determined to be non-matching.

As shown in FIG. 6, it is possible to take the X-ray intensity comparison reference to be 30% or more and it is also possible to designate a comparison threshold value.

In a second method for the spectra comparison means, a method for comparing X-ray spectra is described where a noted element and an X-ray energy region for calculating X-ray intensity of the noted element are designated in advance, and an intensity ratio of a total value of X-ray intensity of a noted element and an X-ray intensity for each element for the X-ray spectra in the database are utilized.

This method is effective when the material content is known in advance and it is wished to determine differences in concentration of the material content.

As shown in FIG. 7, an example is described in the following where determinations are executed taking note of copper and tin.

The noted elements are copper and tin, and the X-ray energy region for calculating X-ray intensity of copper is taken to be 7.8 to 8.3 keV. The X-ray energy region for calculating X-ray intensity of tin is taken to be 24.9 to 25.5 keV. The result of dividing the X-ray intensity for the noted elements by the total value for the X-ray intensity of the noted elements is then taken as the X-ray intensity ratio. In this example, the X-ray intensity of copper is divided by the sum of the X-ray intensities for both copper and tin.

The results of comparing the X-ray spectra are then determined to be not matching when the X-ray intensity ratio changes by more than 10% for copper and 10% for tin.

Non-matching is determined spectra are compared by simply using X-ray intensity when there are regions smaller than the dimensions of the primary beam and regions larger than the dimensions of the primary X-ray beam, but when intensity ratio is adopted as a determination reference, coincidence is determined if a fixed intensity ratio is provided regardless of the size of a region.

A third method provided as a means for comparison is now described where energy where peaks exist is enumerated and X-ray spectra are compared using the presence or absence of each peak.

This method is effective when the material contained in the sample is not-yet known.

Peaks of acquired X-ray spectra are searched for and peak energy is enumerated. Comparison is then made with peak energy enumerated using spectra in the spectra database so that it is determined that the spectra do not match if one peak is different or if a peak does not exist.

This invention brings about the following three effects.

Firstly, regions where there are differences in the element content and differences in the concentration of each element can be easily be divided into groups, while at the same time spectra typifying each group can be acquired.

In the related art, when the contained material was not known in advance, an analysis operation where all of the X-ray spectra were allowed to remain and the intensities of all of the possible elements were collected was carried out over a long period of time. However, if analysis is performed using the present invention, results for typical X-ray spectra are given collectively. The time taken performing spectral analysis can therefore be substantially shortened which brings about substantial benefits from the point of view of efficient use of time.

Secondly, by saving information that has been divided into groups and then displaying this information and information regarding the positions of the measurements in a combined manner, differences in contained elements and differences in concentration can be displayed in an advantageous visual manner. In the case of mapping analysis this is considered to be an obvious function, but for as-yet unknown samples, obtaining analysis information automatically without the aforementioned processing is extremely beneficial.

Thirdly, X-ray spectra having little variation are therefore acquired in the spectra database.

Normally, if the contained elements become clear, the next task is to specify the material.

For example, in the determination of a type of steel such as stainless steel, the type of steel can easily be determined if there is little variation in the X-ray spectra.

It is not realistic to measure for a long period of time at all of the measurement points for mapping analysis, but with this invention it is possible to selectively acquire X-ray spectra with little variation and an accurate analysis operation can therefore be implemented.

In this method, it is not necessary to repeat control of the position of the primary beam when re-acquiring an X-ray spectrum. For example, when an X-ray spectrum is re-acquired after a general measurement, it is no necessary to worry about time being taken up controlling position or about a position not being returned to accurately.

What is claimed is:

1. An X-ray mapping analysis method for putting typical spectra existing in a sample into a database in an X-ray mapping device, which has a spectra database capable of registering X-ray spectra during measurement, comprising the steps of:

starting measurement with the spectra database empty;
irradiating a designated location within a sample with a primary beam using a primary beam control means;
irradiating the sample with the primary beam for a fixed period of time in order to acquire a measurement spectrum;
comparing the X-ray spectrum obtained through measurement and X-ray spectra in the spectra database using a X-ray comparison means;
adding the X-ray spectrum obtained through measurement to the database when no matching X-ray spectra exists in the database;
and repeating measurement at a designated measurement point.

2. The X-ray mapping analysis method according to claim 1,
wherein numbers are assigned to X-ray spectra within the database, results determined by the comparison means are saved as database numbers, and analysis results are displayed using database number information and measurement position information so that distribution of elements can be confirmed visually.

3. The mapping analysis method according to claim 1, wherein X-ray spectra of little variation are obtained by performing measurements again for a long period of time at the same location and storing spectra acquired at such times in the database when no matching X-ray spectra exist within the database.

4. The X-ray mapping analysis method according to claim 1, wherein the spectra comparison means designates a noted element and an X-ray energy region for calculating X-ray intensity of the noted element in advance, compares X-ray intensity of each element of the X-ray spectra in the database and the X-ray intensity of each element in the measured spectra, and determines spectra to be different when change is in excess of a reference quantity.

5. The X-ray mapping analysis method according to claim 1, wherein the spectra comparison means designates a noted element and an X-ray energy region where X-ray intensity of the noted element is calculated in advance, calculates an intensity ratio of a total value of X-ray intensity of a noted element and an X-ray intensity for each element for the X-ray spectra in the database, and, for the measured spectra, calculates a ratio of the total value of X-ray intensity of the noted element and the X-ray intensity of each element, compares the intensity ratio for the same element, and determines that spectra are different spectra when change is in excess of a reference quantity.

6. The X-ray mapping analysis method according to claim 1, wherein the spectra comparison means enumerates energy existing at peaks of X-ray spectra of the data base and of measured spectra and determines different spectra using the presence or absence of each peak.

7. The X-ray mapping analysis method according to claims 1, wherein the primary beam is an X-ray beam.

* * * * *